United States Patent
Murphy

(10) Patent No.: US 12,414,869 B2
(45) Date of Patent: Sep. 16, 2025

(54) STENT DELIVERY SYSTEM AND HANDLING DEVICE FOR A STENT DELIVERY SYSTEM

(71) Applicant: B. Braun Melsungen AG, Melsungen (DE)

(72) Inventor: Bryan Murphy, Bray (IE)

(73) Assignee: B. Braun Melsungen AG, Melsungen (DE)

( * ) Notice: Subject to any disclaimer, the term of this patent is extended or adjusted under 35 U.S.C. 154(b) by 583 days.

(21) Appl. No.: 17/913,955

(22) PCT Filed: Mar. 5, 2021

(86) PCT No.: PCT/EP2021/055640
§ 371 (c)(1),
(2) Date: Sep. 23, 2022

(87) PCT Pub. No.: WO2021/190902
PCT Pub. Date: Sep. 30, 2021

(65) Prior Publication Data
US 2023/0120768 A1    Apr. 20, 2023

(30) Foreign Application Priority Data
Mar. 26, 2020  (EP) ..................... 20165753

(51) Int. Cl.
*A61F 2/95* (2013.01)
*A61F 2/82* (2013.01)
*A61F 2/966* (2013.01)

(52) U.S. Cl.
CPC ............ *A61F 2/9517* (2020.05); *A61F 2/966* (2013.01); *A61F 2002/826* (2013.01)

(58) Field of Classification Search
CPC .. A61F 2/9517; A61F 2/966; A61F 2002/826; A61F 2/95
See application file for complete search history.

(56) References Cited

U.S. PATENT DOCUMENTS

| 8,500,789 B2 | 8/2013 | Wuebbeling et al. |
| 2006/0259124 A1 | 11/2006 | Matsuoka et al. |

(Continued)

FOREIGN PATENT DOCUMENTS

| JP | 2013154220 A | 8/2013 |
| JP | 2017064520 A | 4/2017 |
| WO | 2019053508 A1 | 3/2019 |

OTHER PUBLICATIONS

Office Action received in Japanese Application No. 2022-557979 dated May 14, 2024, with translation, 3 pages.

(Continued)

*Primary Examiner* — Tan-Uyen T Ho
(74) *Attorney, Agent, or Firm* — Christopher A. Rothe; CM Law

(57) ABSTRACT

A stent delivery system includes a handling device having a housing, a thumbwheel rotatably mounted in the housing, and a winding spool rotating with the thumbwheel. A catheter arrangement includes an inner shaft fixed on the housing. An outer sheath is coaxial to the inner shaft. A stent is received between the inner shaft and outer sheath. A pull member engages the outer sheath and is held on the winding spool to be windable. For release of the stent, the outer sheath is displaceable by winding the pull member on the winding spool. A locking mechanism causes, upon reaching at least one defined angle of rotation of the thumbwheel, a locking state of the rotational mobility of the thumbwheel, and thereby of the proximal displaceability of the outer sheath. An unlocking mechanism is in operative connection to the locking mechanism. The locking state is reversible with the unlocking mechanism.

14 Claims, 9 Drawing Sheets

(56) References Cited

U.S. PATENT DOCUMENTS

| | | | |
|---|---|---|---|
| 2007/0168014 A1* | 7/2007 | Jimenez | A61F 2/95 623/1.12 |
| 2012/0022635 A1 | 1/2012 | Yamashita | |
| 2012/0123516 A1 | 5/2012 | Gerdts et al. | |
| 2015/0297378 A1* | 10/2015 | Senness | A61F 2/966 623/1.11 |

OTHER PUBLICATIONS

Search Report received in International Application No. PCT/EP2021/055640 dated Jun. 9, 2021, with translation, 5 pages.

\* cited by examiner

STENT DELIVERY SYSTEM AND HANDLING DEVICE FOR A STENT DELIVERY SYSTEM

CROSS-REFERENCE TO RELATED APPLICATIONS

This application is the United States national stage entry of International Application No. PCT/EP2021/055640, filed Mar. 5, 2021, and claims priority to European Application No. 20165753.3, filed Mar. 26, 2020. The contents of International Application No. PCT/EP2021/055640 and European Application No. 20165753.3 are incorporated by reference herein in their entireties.

FIELD

The invention relates to a stent delivery system and to a handling device for a stent delivery system.

BACKGROUND

It is well known to employ intravascular endoprostheses delivered percutaneously for the treatment of diseases of various body vessels. Such intravascular endoprostheses are commonly referred to as "stents". A stent is a generally longitudinal tubular device of biocompatible material having holes or slots that define a flexible framework that allows radial expansion of the stent, by a balloon catheter or the like, or alternatively by self-expansion due to shape memory characteristics of the material within the body vessel. The flexible framework is configured to allow the stent to be compressed into a smaller outer diameter so that it can be mounted inside a stent delivery system.

The stent delivery system is used to convey the stent to a desired location within the body vessel, and then to release the stent in position. Upon release the stent may self-expand into a larger outer diameter.

WO 2019/053508 A1 discloses a stent delivery system having a handling device and a catheter arrangement. The catheter arrangement comprises an inner shaft, an outer sheath disposed coaxially to the inner shaft, and a stent which is received radially between the inner shaft and the outer sheath. The inner shaft of the catheter arrangement has a proximal end that is fixed to a housing of the handling device. The stent delivery system further comprises a flexible pull member which, with one end, engages on a proximal end of the outer sheath, and, with the other end, is held on a winding spool of the handling device. The winding spool is operatively connected to a thumbwheel that is rotatably mounted inside the housing of the handling device. For release of the stent, the thumbwheel is rotated manually, whereby the winding spool is rotated. The flexible pull member engaging on the winding spool is thereby wound onto the winding spool and, as a result, the outer sheath is displaced relative to the inner shaft in the proximal direction. Due to this proximal retraction of the outer sheath, the stent is released and, thus, can expand within the blood vessel.

SUMMARY

It is the object of the present invention to provide a stent delivery system that allows a simplified and secure handling during the release of the at least one stent. It is a further object of the present invention to provide a handling device for such a stent delivery system, the handling device allowing a simplified and secure handling during the release of the at least one stent.

According to a first aspect, a stent delivery system is provided comprising: a handling device having a housing, a thumbwheel mounted in the housing to be rotatable, and a winding spool rotating together with the thumbwheel; a catheter arrangement having an inner shaft, with a proximal end of the inner shaft fixed on the housing, an outer sheath disposed coaxially to the inner shaft, and having at least one stent which is received radially between the inner shaft and the outer sheath; a flexible pull member which, with one end, engages on a proximal end of the outer sheath and, with the other end, is held on the winding spool to be windable; wherein, for release of the at least one stent, the outer sheath is displaceable relative to the inner shaft in the proximal direction by means of winding the flexible pull member on the winding spool; wherein a locking mechanism is provided and in operative connection to the thumbwheel, which locking mechanism causes, upon reaching at least one defined angle of rotation of the thumbwheel, a locking state of the rotational mobility of the thumbwheel and thereby of the proximal displaceability of the outer sheath, and wherein an unlocking mechanism is provided and in operative connection to the locking mechanism, by means of which unlocking mechanism the locking state is reversible. Owing to the solution according to the invention, an unintended excessive displacement of the outer sheath in the proximal direction during releasing of the at least one stent is counteracted. For that purpose, the locking mechanism is provided. At the same time, the solution according to the invention ensures that the outer sheath, starting from a locking state, is further displaceable in the proximal direction, as required. In that context, the unlocking mechanism is provided. Such a further displacement of the outer sheath in the proximal direction can be desirable and/or required for various reasons. Preferably, the locking mechanism acts exclusively on that direction of rotation of the thumbwheel which causes proximal displacement of the outer sheath. The locking mechanism acts preferably directly on the thumbwheel. Locking of the rotational mobility of the thumbwheel can be in a form-fitting and/or force-fitting manner. Preferably, the locking mechanism is disposed completely inside the housing of the handling device. The at least one defined angle of rotation of the thumbwheel, in which angle the locking mechanism causes the locking, is preferably matched to at least one geometric property of the catheter arrangement. Geometric properties of the catheter arrangement may in particular be axial distances between different components and/or sections of the catheter arrangement, axial length dimensions of such components and/or sections or the like. For example, the at least one defined angle of rotation can be matched to a length of the at least one stent or to a distance of the at least one stent to different components and/or sections of the catheter arrangement. As a result, the rotational mobility of the thumbwheel can be locked, for example, in case that the outer sheath is displaced in the proximal direction over the length of the stent. Subsequently, the locking can be reversed by means of the unlocking mechanism, or be unlocked, to put it in other words. The unlocking mechanism is preferably configured for manual actuation. If this is the case, the unlocking mechanism is preferably disposed completely inside the housing, except for those sections that are provided for manual actuation.

In one embodiment, the locking mechanism is configured such that the locking state is caused after releasing of the at least one stent, wherein the at least one angle of rotation is defined as a function of a proximal displacement of the outer sheath required for that purpose. Accordingly, the rotational mobility of the thumbwheel and, thus, the proximal displaceability of the outer sheath is locked at the point when the at least one stent is released. The at least one angle of rotation of the thumbwheel, in which the locking is caused, is defined correspondingly, i.e. determined by structural features.

In one embodiment, the at least one defined angle of rotation is 360°. In this embodiment of the invention, locking is caused after one complete revolution of the thumbwheel. This complete revolution can take place starting from a delivered state in which the thumbwheel is not displaced, and/or starting from a locked state of the thumbwheel. If the locking mechanism is additionally configured such that the locking is caused after release of the at least one stent, in particular a transmission ratio between the rotation movement of the thumbwheel and the displacing movement of the outer sheath, a length of the at least one stent and/or an axial positioning of the stent on the catheter arrangement are considered in the construction of the locking mechanism for that purpose.

In one embodiment, a plurality of stents are received radially between the inner shaft and the outer sheath and are spaced from each other in the proximal direction, wherein the locking mechanism is configured such that, after releasing of each of the stents, a locking state is caused, wherein the locking states are caused upon reaching a respective defined angle of rotation which is defined as a function of a proximal displacement of the outer sheath required for releasing of the respective stent. In this embodiment of the invention, the stent delivery system is configured as a so-called multi-stent delivery system. Therein, the catheter arrangement includes a plurality of stents spaced from each other in the axial direction and each disposed radially between the inner shaft and the outer sheath. The locking mechanism is configured such that the locking is caused repeatedly, namely after releasing of each of the stents, wherein in each case a corresponding unlocking is effected by means of the unlocking mechanism before releasing of the next stent. Owing to this embodiment of the invention, an unintended displacement of the outer sheath in the proximal direction so far that an undesired release of one of the stents occurs is prevented. Therefore, the locking mechanism does not only lock at a single defined angle of rotation of the thumbwheel, but at different (absolute) angles of rotation.

In one embodiment, the defined angles of rotation are integral multiples. In this context, the defined angles of rotation are to be understood as absolute angles of rotation. In other words, the locking mechanism is in this embodiment of the invention configured such that the locking is caused repeatedly after one and the same relative rotation movement of the thumbwheel. For example, this occurs after a quarter, a half, a three-quarters and a complete revolution of the thumbwheel etc. Preferably, the locking mechanism is configured such that the locking is caused repeatedly after in each case one complete revolution of the thumbwheel.

In one embodiment, the locking mechanism includes a rotatably mounted driving gear which is driven by the thumbwheel, a rotatably mounted driven gear which is driven by the driving gear, and a movably mounted locking member on which the driven gear comes into abutment upon reaching the at least one defined angle of rotation of the thumbwheel, thereby producing the locking state, wherein the locking member is displaceable relative to the driven gear by means of the unlocking mechanism for reversing the locking state. Hereby, a particularly simple and robust construction of the locking mechanism can be achieved. The driving gear is connected to the thumbwheel preferably in a torque-transmitting manner. Preferably, the driving gear is oriented coaxially to the thumbwheel, wherein the thumbwheel and the driving gear are rotatable about a common rotation axis. The driven gear is driven by the driving gear and, thus, indirectly by the thumbwheel. Upon reaching the at least one defined angle of rotation of the thumbwheel, the driven gear comes to abutment on the locking member, in particular radially, tangentially and/or axially, whereby the locking is obtained. The locking member is displaceable relative to the driven gear for reversing the locking, i.e. for unlocking. For that purpose, the locking member can be mounted to be movable in a linear, rotational and/or pivoting manner.

In one embodiment, the locking mechanism includes a first spring element which applies a spring force to the locking member to counteract displacing of the locking member by means of the unlocking mechanism. By this means, unintended unlocking can be counteracted in a simple and particularly effective manner.

In one embodiment, the driving gear is provided integrally with the thumbwheel. This allows a particularly simple construction of the locking mechanism. Namely, owing to the design of the drive gear in one piece with the thumbwheel, a required number of component parts can be reduced.

In one embodiment, the driving gear and the driven gear form a Geneva drive gear mechanism. Accordingly, the drive gear and the driven gear form a stepping or indexing gear in the form of a Geneva drive gear mechanism. The principles of the structural design and function of such a Geneva drive gear mechanism are in any case well-known to a person skilled in the field of drive engineering. For reasons of brevity, further details in that relation are not discussed herein.

In one embodiment, the driven gear has an abutment portion protruding radially upward from the outer circumference thereof, which abutment portion, upon reaching the at least one defined angle of rotation, abuts a counter-abutment portion on the locking member. In this embodiment of the invention, locking is accordingly achieved by abutment of the abutment portion on the counter-abutment portion. The abutment portion is a protrusion of the outer circumference of the driven gear. Upon reaching the at least one defined angle of rotation of the thumbwheel, the abutment portion and the counter-abutment portion interact in a form-fitting manner. Thereby, a further rotation movement of the driven gear and, finally of the thumbwheel cooperating with the drive gear is prevented.

In one embodiment, the locking member is a pivotable locking lever. Thereby, a further simplified construction of the locking mechanism can be achieved. The locking lever is pivotable between different positions by means of the unlocking mechanism.

In one embodiment, the unlocking mechanism includes a movably mounted unlocking member with an actuator portion which is provided for manual actuation, and with a controller portion which cooperates with the locking mechanism. The unlocking member can be mounted to be movable in a linear, rotational and/or pivoting manner. The unlocking member is preferably mounted on a section of the housing provided for that purpose. With the exception of the actuator portion, the unlocking member is preferably disposed completely within the housing. By means of actuation of the actuator portion, the unlocking member is movable for unlocking the locking mechanism between different positions. Herein, the controller portion cooperates with the locking mechanism, preferably with the locking member.

In one embodiment, the unlocking mechanism includes a second spring element which applies a spring force to the unlocking member to counteract displacing of the unlocking member by means of actuating the actuator portion. Thereby, unintended actuation of the unlocking member and, thus, unintended unlocking of the locking mechanism is counteracted. Moreover, the second spring element causes an advantageous return of the unlocking member such that the latter returns to its initial position supported by spring force after an unlocking actuation.

In one embodiment, the unlocking member is a pivotable unlocking lever. Thereby, a particularly simple construction of the unlocking mechanism is achieved. The actuator portion can be disposed on one end of the unlocking lever. The controller portion can be disposed on the other end of the unlocking lever. If the locking member is configured as a pivotable locking lever, the unlocking lever is preferably mounted to be pivotable in the opposite direction thereto. Thereby, particularly advantageous leverage ratios can be achieved between the locking lever and the unlocking lever.

According to a second aspect, a handling device for a stent delivery system is provided, the handling device having a housing, a thumbwheel mounted in the housing to be rotatable, and a winding spool rotating together with the thumbwheel, wherein a locking mechanism is provided and in operative connection to the thumbwheel, which locking mechanism causes, upon reaching at least one defined angle of rotation of the thumbwheel, a locking state of the rotational mobility of the thumbwheel, and in that an unlocking mechanism is provided and in operative connection to the locking mechanism, by means of which unlocking mechanism the locking state is reversible. To avoid repetitions, referral and explicit reference is made to the description of the first aspect and its embodiments. The explanations given within the scope of disclosure in relation to the stent delivery system and the handling device therein, apply correspondingly to the handling device according to the second aspect.

BRIEF DESCRIPTION OF THE DRAWINGS

In the following, an embodiment of the invention will be described in detail with reference to the drawings. Throughout the drawings, the same elements will be denoted by the same reference numerals.

DETAILED DESCRIPTION

Figure 1:
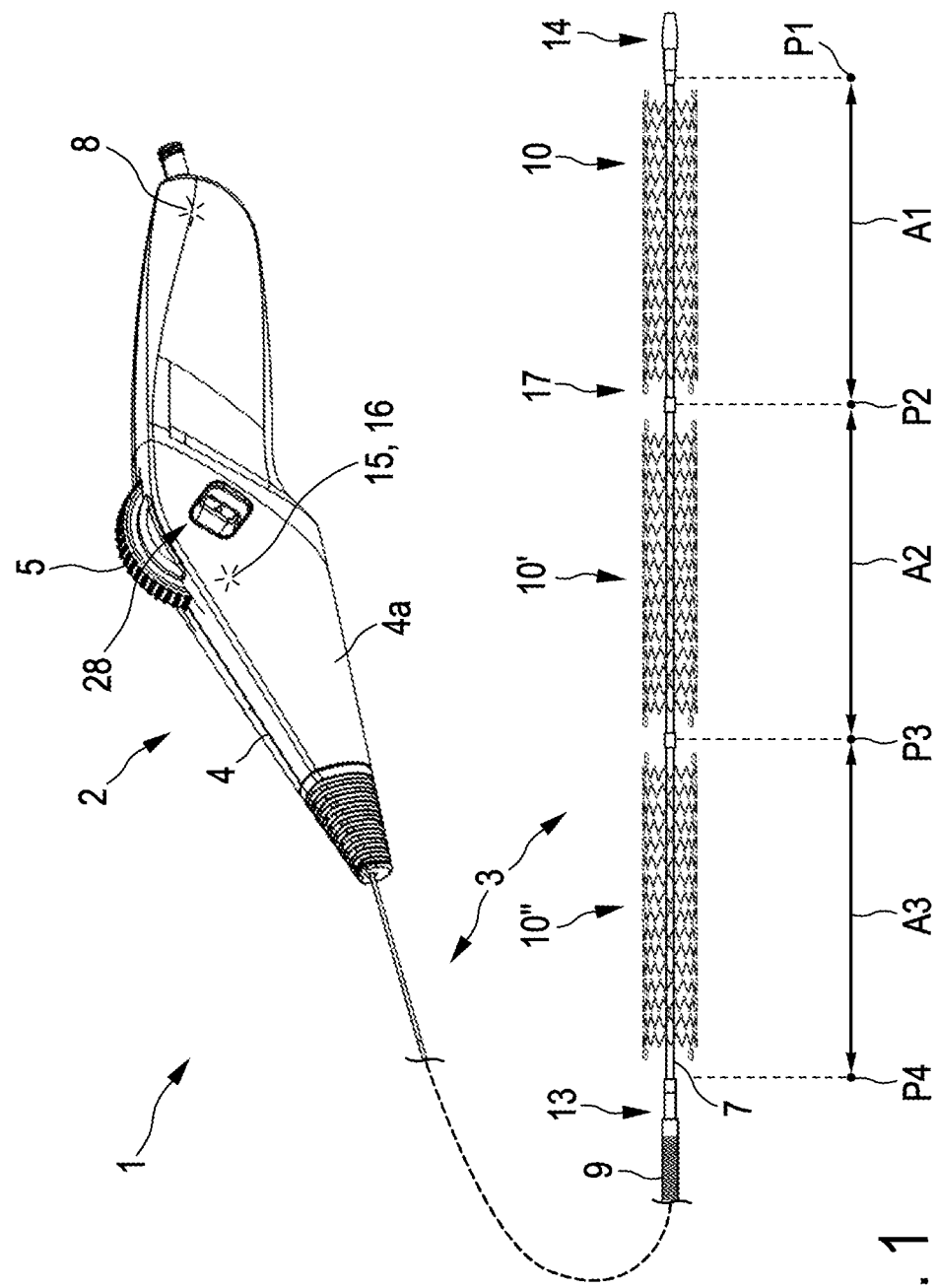
FIG. 1 is an isometric view an embodiment of a stent delivery system according to the invention, including one embodiment of a handling device according to the invention and a catheter arrangement with a plurality of stents, wherein the catheter arrangement is illustrated with partial sections.
Figure 2:
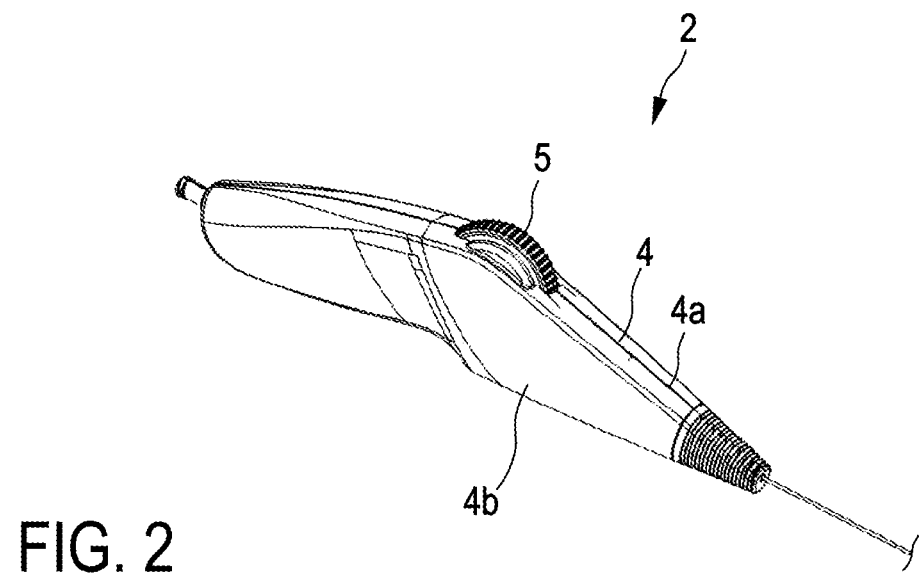
FIG. 2 shows the stent delivery system according to FIG. 1 in the region of the handling device in a further isometric view.

According to FIG. 1, a stent delivery system 1 comprises a handling device 2 and a catheter arrangement 3. The stent delivery system 1 is intended for use in the treatment of stenosis in blood vessels.

Figure 3:
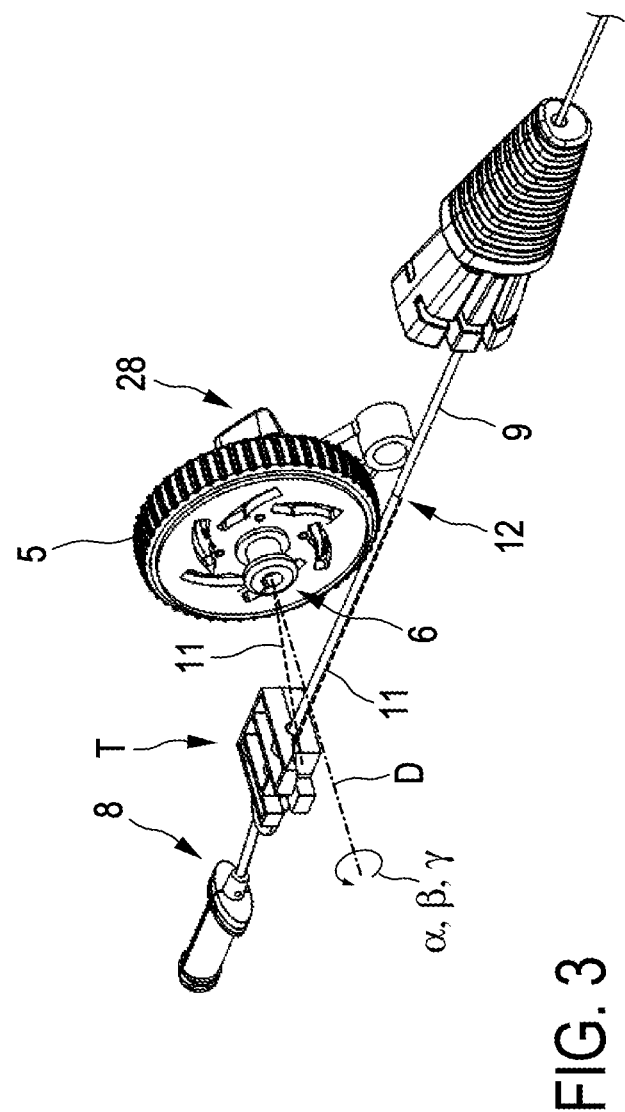
FIG. 3 shows the stent delivery system according to FIGS. 1 and 2 in a view corresponding to FIG. 2 with individual components and/or sections of the handling device hidden in the drawing.

The handling device 2 has a housing 4 with a thumbwheel 5 mounted in the housing 4 to be rotatable and a winding spool 6 rotating together with the thumbwheel 5 (FIG. 3). The catheter arrangement 3 has an inner shaft 7 and an outer sheath 9 disposed coaxially to the inner shaft 7. A proximal end 8 of the inner shaft 7 is fixed on the housing 4 at least indirectly and in a generally well-known manner. Further, the catheter arrangement 3 includes at least one stent 10 which is received radially between the inner shaft 7 and the outer sheath 9 in a condition of the catheter arrangement not graphically illustrated in more detail. Moreover, the stent delivery system 1 includes a flexible pull member 11 which, with one end, engages on a proximal end 12 of the outer sheath 9 and, with the other end, is held on the winding spool 6 to be windable. With reference to FIG. 3, the flexible pull member 11 is indicated merely schematically and illustrated in dashed lines. For release of the at least one stent 10, the outer sheath 9 is displaceable relative to the inner shaft 7 in the proximal direction by means of winding the flexible pull member 11 on the winding spool 6. The release takes place from a displacement position of the outer sheath 9 not illustrated in more detail, wherein a distal end 13 of the outer sheath 9 is essentially flush with a distal end 14 of the inner shaft 7. In this condition, the at least one stent 10 is compressed in the radial direction between an outer shell surface of the inner shaft 7 and an inner shell surface of the outer sheath 9. Following the above-mentioned retraction of the outer sheath 9 in the proximal direction, the at least one stent 10 is released and thereby may expand in the radial direction. With reference to FIG. 1, a corresponding released and expanded condition of the at least one stent 10 is illustrated.

Figure 4:
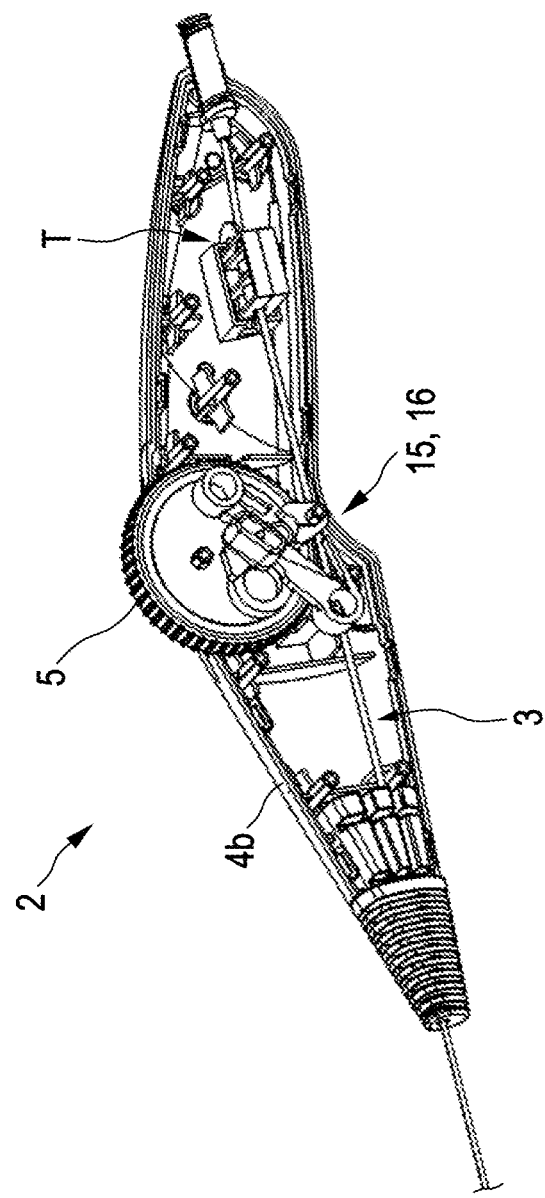
FIG. 4 shows a further isometric view in the region of the handling device with a housing half of a housing of the handling device hidden in the drawing and a direction of viewing on a locking mechanism and an unlocking mechanism.
Figure 5:
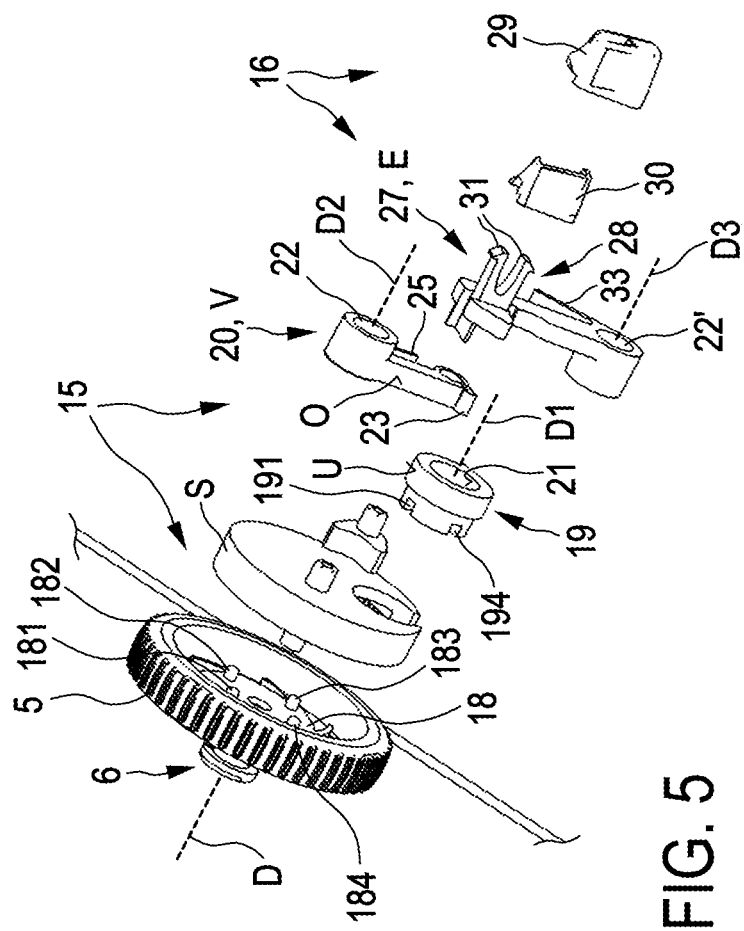
FIGS. 5, 6 and 7 show different isometric exploded views in the region of the locking and unlocking mechanism.
Figure 6:
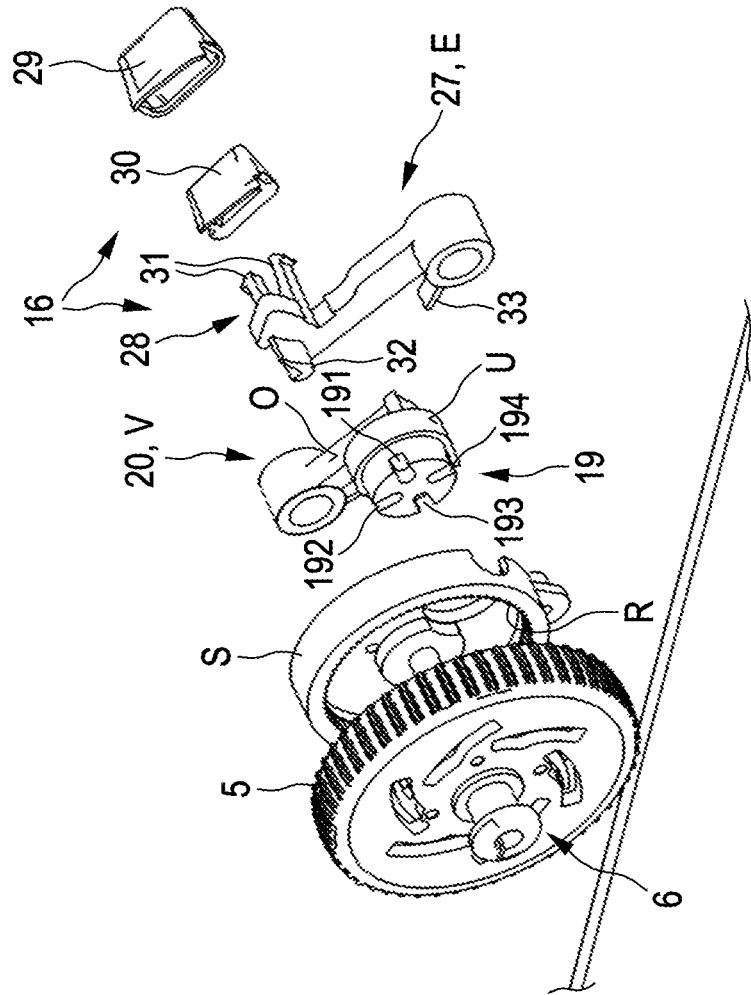
Figure 7:
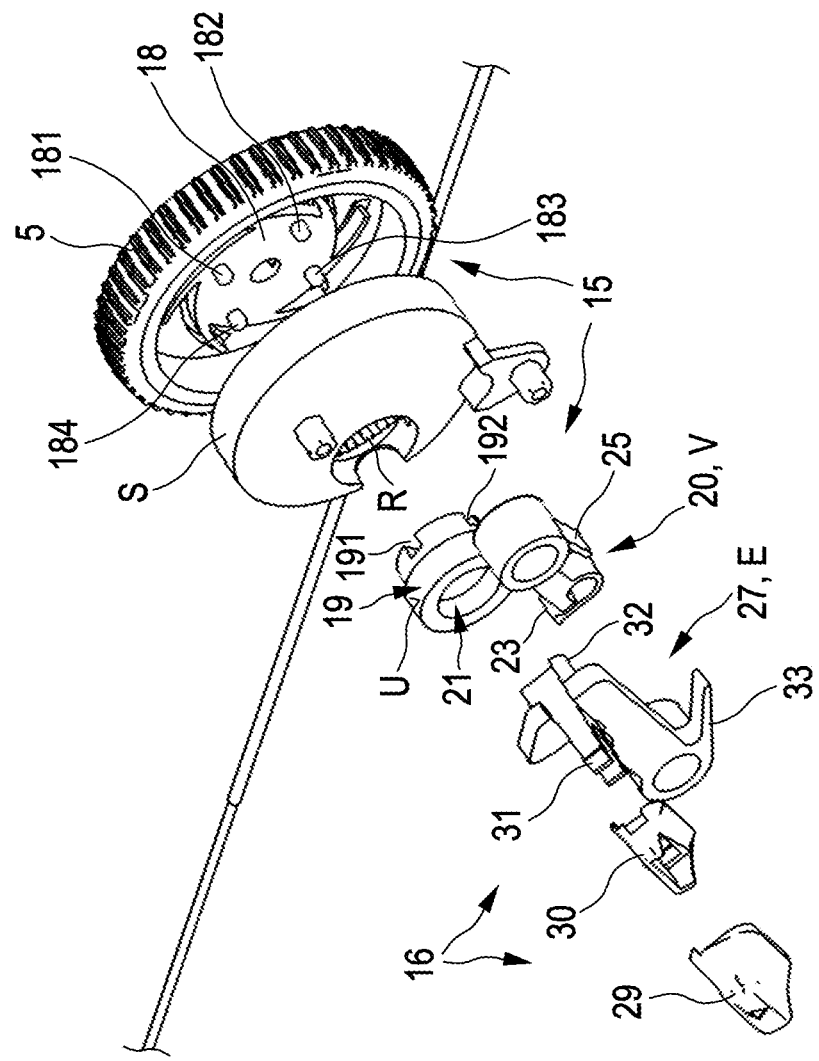
Figure 8:
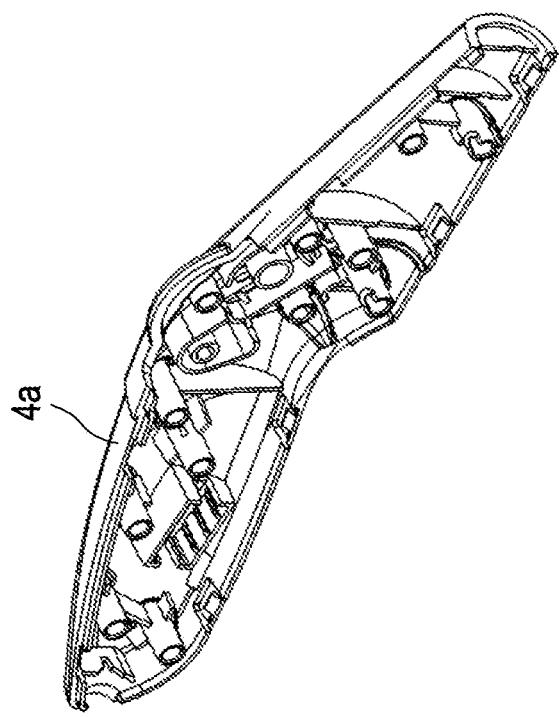
FIG. 8 is an isometric view of the housing half hidden in the drawing of FIG. 4 with a direction of viewing on a housing interior side.

As illustrated in particular with reference to FIG. 4, the stent delivery system 1 includes a locking mechanism 15 in operative connection to the thumbwheel 5 and an unlocking mechanism 16 in operative connection to the locking mechanism 15. The locking mechanism 15 causes, upon reaching at least one defined angle α of rotation of the thumbwheel 5, a locking state of the rotational mobility of the thumbwheel 5 and thus of the proximal displaceability of the outer sheath 9. By means of the unlocking mechanism 16 the above mentioned locking can be reversed.

By means of the locking mechanism 15, an unintended further displacement of the outer sheath 9 in the proximal direction upon actuation of the thumbwheel 5 is counteracted. For that purpose, the mobility of the thumbwheel 5 and of the outer sheath 9 are locked using the locking mechanism 15 in a manner that will be described in more detail below. The unlocking mechanism 16 is intended for unlocking such that, after completed locking, a further actuation of the thumbwheel 5 and, thus, a further displacement of the outer sheath 9 can be effected.

Before discussing the specific configuration of the handling device 2 and the catheter arrangement 3, first the further features of the locking and unlocking mechanisms 15, 16 are explained in detail.

In the embodiment shown, the locking mechanism 15 is configured such that the locking state of the thumbwheel 5 is caused after release of the at least one stent 10. Accordingly, the angle of rotation α defined by construction, in which angle the locking mechanism 15 is active and the thumbwheel 5 is locked, respectively, is matched to the proximal displacement of the outer sheath 9 required for release of the at least one stent 10.

Releasing of the at least one stent 10 takes place starting from a displacement position P1 of the outer sheath 9, in which position the distal end 13 of the outer sheath 9 is essentially flush with a distal end 14 of the inner shaft 7 (FIG. 1). Starting from this first displacement position P1, the outer sheath 9 is moved relative to the inner shaft 7 to a proximally retracted second displacement position P2. This occurs by means of the above mentioned actuation of the thumbwheel 5 and the winding of the flexible pull member 11 on the winding spool 6 accompanied therewith. In the second displacement position P2, the distal end 13 of the outer sheath 9 is displaced in the proximal direction beyond a proximal end 17 of the stent 10 to a minor extent (FIG. 1). In the present case, the locking mechanism 15 is configured such that the defined angle of rotation α is reached there and, thus, the locking state is caused when the distal end 13 reaches the second displacement position P2. This is to prevent that the thumbwheel 5 can be actuated in rotation over the defined angle of rotation α and, thereby, the outer sheath 9 can be displaced over the distal end 13 in the proximal direction over the second displacement position P2.

In the embodiment shown, the locking mechanism 15 is moreover configured such that the defined angle of rotation α is 360°. In other words, the thumbwheel 5 is locked upon reaching on complete revolution. A structural design of the locking mechanism 15 required therefor considers in particular an axial distance A1 between the first displacement position P1 and the second displacement position P2 and a transmission ratio between the rotation movement of the thumbwheel 5 and the displacing movement of the winding spool 6.

As is further apparent with reference to FIG. 1, the catheter arrangement 3 in the embodiment shown, includes a plurality of stents 10, 10', 10". In that context, in addition to the stent 10 which may also be referred to as first stent 10, a second stent 10' and a third stent 10" are provided. The second stent 10' and the third stent 10" are received in the radial direction between the inner shaft 7 and the outer sheath 9, in a manner corresponding to the first stent 10, and releasable by means of a proximal displacement of the outer sheath 9, wherein with reference to FIG. 1, again a released and expanded condition of the stents 10', 10" is illustrated in the drawing. The second stent 10' is spaced in the proximal direction from the first stent 10. The third stent 10" is spaced in the proximal direction from the second stent 10'.

In the embodiment shown, the locking mechanism 15 is moreover configured such that, after release of each of the stents 10, 10', 10", a locking state is caused, wherein the locking state is reached after reaching a respective defined angle of rotation, namely the angle of rotation α and furthermore the angles of rotation β, γ (FIG. 3). The further angles of rotation β, γ are matched to the proximal displacement of the outer sheath 9 required for releasing of the respective stent 10', 10" in a manner corresponding to the angle of rotation α. Accordingly, the locking mechanism 15 is not merely effective for causing locking upon reaching the second displacement position P2, but also upon reaching the third displacement position P3 and a fourth displacement position P4 (FIG. 1). In the third displacement position P3, the distal end 13 of the outer sheath is located in the axial direction between a proximal end of the second stent 10' and a distal end of the third stent 10". In the fourth displacement position P4, the distal end 13 of the outer sheath is displaced in the proximal direction to a minor extent beyond a proximal end of the third stent 10". The third displacement position P3 corresponds to the further defined angle of rotation β. The fourth displacement position P4 corresponds to the further defined angle of rotation γ. Thus, the further angles of rotation β, γ are defined in a manner corresponding to the angle of rotation α, in particular as a function of the further axial distances A2, A3. The further axial distance A2 extends between the second displacement position P2 and the third displacement position P3. The further axial distance A3 extends between the third displacement position P3 and the fourth displacement position P4.

In the embodiment shown, the further angles of rotation β, γ are integral multiples of the angle of rotation α. Accordingly, the locking mechanism 15 causes locking in each case after one complete revolution of the thumbwheel 5. It is prevented thereby that the outer sheath 9, after release of the first stent 10, is displaced in the proximal direction—and thus beyond the second displacement position P2—unintentionally. Since this movement could result in an unintended release of the second stent 10'. Instead the locking mechanism 15 causes locking, upon reaching the second displacement position P2. For further displacement of the outer sheath 9 to release the second stent 10', first an unlocking step by means of the unlocking mechanism 16 has to be effected. The same applies after release of the second stent 10'. That is, upon reaching the third displacement position P3, the locking mechanism 15 causes a new locking state. This locked condition has to be reversed before releasing of the third stent 10' using the unlocking mechanism 16.

The configuration of the locking mechanism 15 and the unlocking mechanism 16 provided in the embodiment shown, will be explained in detail below, in particular with reference to FIGS. 5, 6, 7 and 10.

In the embodiment shown, the locking mechanism 15 includes a rotatably mounted driving gear 18, a rotatably mounted driven gear 19 and a movably mounted locking member 20.

The driving gear 18 is driven to rotation by the thumbwheel 5. In that context, in the embodiment shown, the driving gear 18 is provided integrally with the thumbwheel 5 and, thus, mounted in the housing 4 to be movable about a rotation axis D coaxially thereto. The winding spool 6 is likewise coaxial to the thumbwheel 5 and, thus, also disposed coaxial to the driving gear 18 and, thus, likewise rotatable about the rotation axis D. The above described angles of rotation α, β, γ refer to the rotation axis D (FIG. 3).

The driven gear 19 is driven by the driving gear 18. The operative connection required therefor between the driving gear 18 and the driven gear 19 may in general provide a continuous or intermittent transmission of the rotational movement of the driving gear 18 to the driven gear 19, wherein in the present case an intermittent transmission is provided and will be described in more detail below. The driven gear 19 is mounted on the housing 4 to be rotatable about a rotation axis D1 which may also be referred to as first rotation axis D1. For this purpose, the housing 4, more precisely: a left housing half 4a of the housing 4, has a first bearing journal Z1 which cooperates with a bearing bore 21 of the driven gear 19. The first rotation axis D1 is oriented offset in parallel to the rotation axis D of the driving gear 18. Furthermore, in the present case, a right housing half 4b is provided. The two housing halves 4a, 4b are joined together, thereby forming the housing 4.

Figure 9:
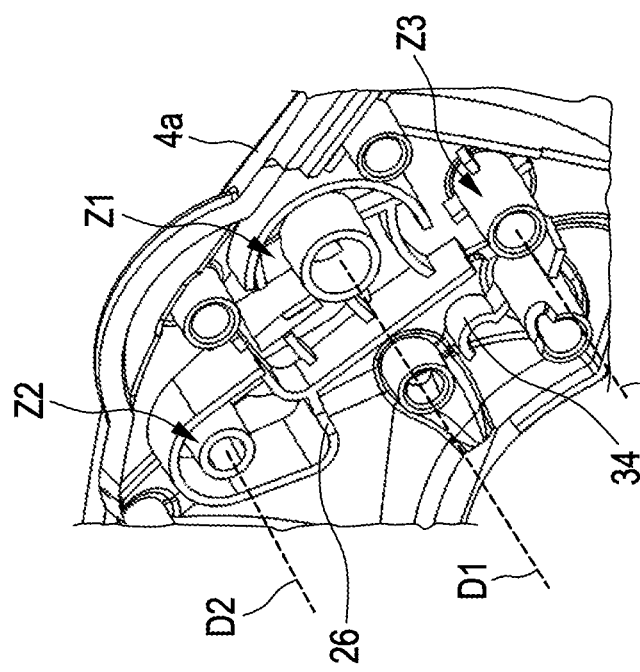
FIG. 9 is an enlarged detail illustration of the housing interior side.

The locking member 20 and the driven gear 19, upon reaching the angles of rotation α, β, γ, cooperate in a form-fitting manner, thereby forming the locking state in a way that will be described in more detail below. Therein, the locking member 20 is displaceable relative to the driven gear 19 by means of the unlocking mechanism 16 for reversing the locking state, starting from a locked condition in which the driven gear 19 cooperates in a form-fitting manner with the locking member 20. In the present case, the locking member 20 is mounted on the left housing half 4a to be pivotable about a rotation axis D2 which may also be referred to as second rotation axis D2. Therefore, the left housing half 4a has a second bearing journal Z2 (FIG. 9) which cooperates with a bearing bore 22 of the locking member 20.

Figure 10:
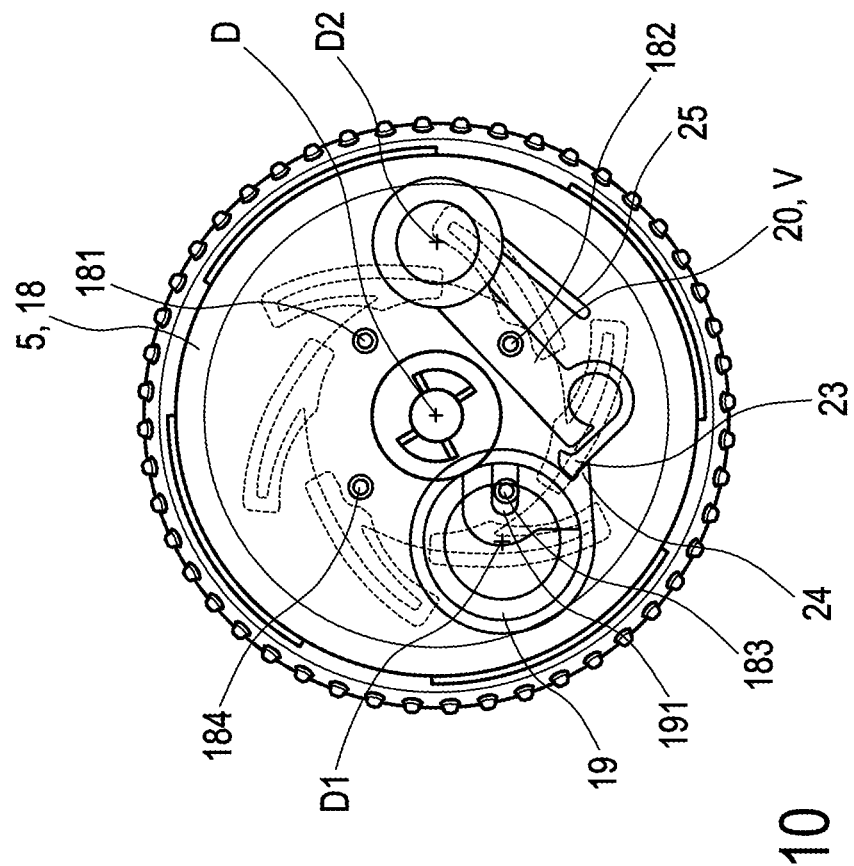
FIG. 10 is a detail view of the locking mechanism in an axial direction of viewing and in a locked condition.

In the embodiment shown, the locking member 20 is a locking lever V that is pivotable about the second rotation axis D2. The locking lever V has a counter-abutment portion 23 located in a front end region facing away from the second rotation axis D2 and, thus, from the bearing bore 22, which lever in the locked condition cooperates with an abutment portion 24 of the driven gear 19 (FIG. 10). The abutment portion 24 protrudes radially upward from the outer circumference U of the driven gear 19. In this manner, the abutment portion 24 provides a radial projection which may also be referred to as a lug.

Moreover, the locking mechanism 15 includes a first spring element 25. The first spring element 25 applies a spring force to the locking member 20 to counteract displacement by means of the unlocking mechanism 16. In other words, the locking lever V is pre-tensioned by the first spring element 25 clockwise about the second rotation axis D2, in relation to the drawing plane of FIG. 10.

In the embodiment shown, the first spring element 25 is provided integrally with the locking member 20. The first spring element 25 is designed as a type of leaf spring and resiliently supported on a support portion 26 (FIG. 9) of the left housing half 4a provided for that purpose.

The driving gear 18 and the driven gear 19 form a Geneva drive gear mechanism 18, 19, in the embodiment shown, whereby the above mentioned intermittent transmission of the rotational movement of the thumbwheel 5 to the driven gear 19 is obtained. The Geneva drive gear mechanism 18, 19 may also be referred to as a stepping or indexing gear and has a function principle which is common knowledge for a person skilled in the art of drive engineering. Accordingly, the driving gear 18 is provided with a plurality of coupling pins 181, 182, 183, 184. The driven gear 19 includes a plurality of coupling grooves 191, 192, 193, 194, which engage with a respective one of the coupling pins 181 to 184 for transmission of the rotational movement between the driving gear 18 and the driven gear 19, cooperate in sliding movement and subsequently disengage. In the present case, four coupling pins 181 to 184 and four coupling grooves 191 to 194 are provided. These parts are in each case disposed offset by 90° in relation to each other about the rotation axis D and the first rotation axis D1, respectively, of the driving gear 18 and the driven gear 19, respectively. However, such a configuration is not mandatory. Accordingly, more or fewer coupling pins and/or coupling grooves may be provided.

The unlocking mechanism 16 includes a movably mounted unlocking member 27. In the embodiment shown, the unlocking member 27 is a pivotable unlocking lever E which is mounted to be pivotable about a third rotation axis D3 on the left housing half 4a. The left housing half 4a has for that purpose a third bearing journal Z3 which cooperates with a bearing bore 22' of the unlocking lever E. The third rotation axis D3 is oriented parallel to the second rotation axis D2, the first rotation axis D1 and the rotation axis D of the thumbwheel 5. The unlocking lever E includes an actuator portion 28 which is provided for manual actuation and protrudes laterally from a recess of the housing 4, not described in more detail, in the ready-for-use condition of the housing 4 (FIG. 1). The actuator portion 28 is provided with a rubber element 29 for ergonomic operation, which rubber element is attached to an intermediate piece 30. The intermediate piece 30 is latched in a form-fitting manner with a connector portion 31 of the unlocking lever E. However, such a configuration is not mandatory. Accordingly, in an embodiment not shown, neither the rubber element 29 nor the intermediate piece 30 is provided.

Further, the unlocking lever E includes a controller portion 32 which cooperates with a section of the locking lever V provided for that purpose for unlocking the locking mechanism 15. The controller portion 32 is disposed on a front end region of the unlocking lever E facing away from the third rotation axis D3 and cooperates with an upper side O of the locking lever V for unlocking.

Further, the unlocking mechanism 16 includes a second spring element 33 which applies a spring force to the unlocking lever E to counteract displacing of the unlocking lever E by means of actuating the actuator portion 28. The second spring element 33 is provided integrally with the unlocking lever E and designed as a type of leaf spring, in the embodiment shown. In the ready-for-use condition, the second spring element 33 is supported on a support portion 34 (FIG. 9) of the left housing half 4a provided for that purpose.

The further mode of function of the locking mechanism 15 and the unlocking mechanism 16 will be explained below in particular with reference to FIG. 10. What is shown there is a locked condition in which the rotational mobility of the thumbwheel 5 about the rotation axis D and, thus, the proximal displaceability of the outer sheath 9 are locked. The locked condition is assumed, in the present case, (initially) in the first displacement position P1 (FIG. 1). In said locked condition, the abutment portion 24 of the driven gear 19 and the counter-abutment portion 23 of the locking lever V cooperate in a form-fitting manner, thereby forming the locking state. As a result of said form-fitting feature, further rotation of the driven gear 19 about the first rotation axis D1 is inhibited, in any case counterclockwise, in relation to the drawing plane of FIG. 10. Accordingly, as well further clockwise rotation of the driving gear 18 and, thus, also of the thumbwheel 5 about the rotation axis D is inhibited. This due to the fact that, as a result of the abutment provided with the locking lever V, no further relative movement between the coupling pin 183 and the coupling groove 191 is possible. Accordingly, before a further rotational actuation of the thumbwheel 5, an initial unlocking by means of the unlocking mechanism 16 needs to be effected.

For that purpose, the actuator portion 28 of the unlocking lever E is actuated manually. With reference to the drawing plane of FIG. 1, the actuator portion 28 is therefore pushed from obliquely above in the proximal direction. What is caused thereby is a pivoting move of the unlocking lever E about the third rotation axis D3. This pivoting move is directed clockwise in relation to the drawing plane of FIG. 10. In doing so, the controller portion 32 of the unlocking lever E comes to abutment on the upper side O of the locking lever V. The latter is thereby displaced counterclockwise about the second rotation axis D2, whereby the counter-abutment portion 23 is displaced in the radial direction relative to the abutment portion 24 and is disengaged therefrom. The actuation of the actuator portion 28 is maintained and the thumbwheel 5 is displaced clockwise about the rotation axis D, in relation to the drawing plane of FIG. 10. Once the abutment portion 24 is thereby moved past the counter-abutment portion 23, the actuation of the actuator portion 28 can be removed. As a result, both the unlocking lever E and the locking lever V return to their initial positions owing to spring force.

During the further rotational actuation of the thumbwheel 5, the third coupling pin 183 cooperates in sliding movement with the first coupling groove 191 and moves on a circular path oriented concentric to the rotation axis D. The driven gear 19 is thereby driven counterclockwise about the first rotation axis D1. Once the third coupling pin 183 is disengaged from the first coupling groove 191 and the thumbwheel 5 is displaced further about the rotation axis D, the second coupling pin 182 engages on a further one of the coupling grooves 191 to 194. Thereby, the driven gear 19 is displaced with each engagement by 90° about the first rotation axis D1. After a complete revolution of the thumbwheel 5—and, thus upon reaching the defined angle of rotation α—the abutment portion 24 again comes to abutment on the counter-abutment portion 23, whereby a new locking state is reached. In the present case, said locking state is reached upon reaching the second displacement position P2 of the outer sheath 9. Subsequently, a new unlocking may take place. For release of the second stent 10, the thumbwheel 5 can be displaced by a further complete revolution about the rotation axis D, until a new locking takes place. This will occur upon reaching the third displacement position P3 and, thus, upon reaching the defined angle of rotation β. Subsequently, for release of the third stent 10″, a new unlocking and a new rotational actuation of the thumbwheel 5 by a further complete revolution until reaching the fourth displacement position P4 and, thus, upon reaching the defined angle of rotation γ may take place.

Furthermore, in the embodiment shown, the handling device 2 includes a ratchet mechanism counteracting a rotational actuation of the thumbwheel 5 counterclockwise. The ratchet mechanism includes a ratchet surface R which is provided on a so-called stator wheel S and cooperates with a plurality of ratchet elements, not described in more detail, and disposed on the thumbwheel 5. Neither the ratchet mechanism nor the stator wheel S is mandatory in view of the present invention, so that for reasons of brevity further explanations thereto are omitted.

Furthermore, in the embodiment shown, the handling device includes a deflecting and tensioning device T which is disposed in the axial direction of the catheter arrangement 3 between the thumbwheel 5 and the proximal end 8 of the inner shaft 7. The deflecting and tensioning device T is intended for deflecting and tensioning of the flexible pull member 11 (FIG. 3). However, the deflecting and tensioning device T is not mandatory. Therefore, a more detailed description thereof is omitted for reasons of brevity.

The invention claimed is:

1. A stent delivery system, comprising:
    a handling device having a housing, a thumbwheel mounted in the housing to be rotatable, and a winding spool rotating together with the thumbwheel;
    a catheter arrangement having an inner shaft, with a proximal end of the inner shaft fixed on the housing, an outer sheath disposed coaxially to the inner shaft, and having at least one stent which is received radially between the inner shaft and the outer sheath; and
    a flexible pull member which, with one end, engages on a proximal end of the outer sheath and, with the other end, is held on the winding spool to be windable, wherein:
    for release of the at least one stent, the outer sheath is displaceable relative to the inner shaft in a proximal direction by winding the flexible pull member on the winding spool,
    a locking mechanism is provided and in operative connection to the thumbwheel, which locking mechanism causes, upon reaching at least one defined angle of rotation of the thumbwheel, a locking state of a rotational mobility of the thumbwheel and thereby of a proximal displaceability of the outer sheath,
    an unlocking mechanism is provided in operative connection to the locking mechanism, the locking state being reversible with the unlocking mechanism,
    the locking mechanism includes a rotatably mounted driving gear which is driven by the thumbwheel, a rotatably mounted driven gear which is driven by the driving gear, and a movably mounted locking member on which the driven gear comes into abutment upon reaching the at least one defined angle of rotation of the thumbwheel, thereby producing the locking state, and
    the locking member is displaceable relative to the driven gear by the unlocking mechanism for reversing the locking state.

2. The stent delivery system according to claim 1, wherein the locking mechanism is configured such that the locking state is caused after releasing of the at least one stent, wherein the at least one defined angle of rotation is defined as a function of a proximal displacement of the outer sheath required for that purpose.

3. The stent delivery system according to claim 1, wherein the at least one defined angle of rotation is 360°.

4. The stent delivery system according to claim 1, wherein the at least one stent comprises a plurality of stents that are received radially between the inner shaft and the outer sheath and are spaced from each other in the proximal direction, wherein the locking mechanism is configured such that, after releasing of each of the plurality of stents, a locking state is caused, wherein for each stent, the locking state is caused upon reaching a defined angle of rotation which is defined as a function of a proximal displacement of the outer sheath required for releasing said stent.

5. The stent delivery system according to claim 4, wherein the defined angles of rotation are integral multiples.

6. The stent delivery system according to claim 1, wherein the locking mechanism includes a first spring element which applies a spring force to the locking member to counteract displacing of the locking member by the unlocking mechanism.

7. The stent delivery system according to claim 1, wherein the driving gear is provided integrally with the thumbwheel.

8. The stent delivery system according to claim 1, wherein the driving gear and the driven gear form a Geneva drive gear mechanism.

9. The stent delivery system according to claim 1, wherein the driven gear has an abutment portion protruding radially upward from the outer circumference thereof, which abutment portion, upon reaching the at least one defined angle of rotation, abuts on a counter-abutment portion of the locking member.

10. The stent delivery system according to claim 1, wherein the locking member is a pivotable locking lever.

11. The stent delivery system according to claim 1, wherein the unlocking mechanism includes an unlocking member that is movably mounted, the unlocking member comprising an actuator portion for manual actuation and a controller portion that cooperates with the locking mechanism.

12. The stent delivery system according to claim 11, wherein the unlocking mechanism includes a second spring element that applies a spring force to the unlocking member to counteract displacement of the unlocking member by actuating the actuator portion.

13. The stent delivery system according to claim 11, wherein the unlocking member is a pivotable unlocking lever.

14. A handling device for a stent delivery system, the handling device comprising:
   a housing;
   a thumbwheel mounted in the housing to be rotatable;
   a winding spool rotating together with the thumbwheel;
   a locking mechanism; and
   an unlocking mechanism,
   the locking mechanism being in operative connection to the thumbwheel,
   the locking mechanism causing, upon reaching at least one defined angle of rotation of the thumbwheel, a locking state of a rotational mobility of the thumbwheel,
   the unlocking mechanism being in operative connection to the locking mechanism, the locking state being reversible with the unlocking mechanism.

\* \* \* \* \*